(12) United States Patent
DeAscanis et al.

(10) Patent No.: US 9,599,537 B2
(45) Date of Patent: Mar. 21, 2017

(54) INTERNAL INSPECTION OF MACHINERY BY STITCHED SURFACE IMAGING

(71) Applicant: Siemens Energy, Inc., Orlando, FL (US)

(72) Inventors: Joshua DeAscanis, Oviedo, FL (US); William D. Clark, Orlando, FL (US); Clifford Hatcher, Jr., Orlando, FL (US); Forrest R. Ruhge, Orlando, FL (US)

(73) Assignee: SIEMENS ENERGY, INC., Orlando, FL (US)

( * ) Notice: Subject to any disclaimer, the term of this patent is extended or adjusted under 35 U.S.C. 154(b) by 315 days.

(21) Appl. No.: 14/526,609

(22) Filed: Oct. 29, 2014

(65) Prior Publication Data

US 2015/0054939 A1    Feb. 26, 2015

Related U.S. Application Data

(63) Continuation-in-part of application No. 13/972,000, filed on Aug. 21, 2013, now Pat. No. 9,116,071.

(51) Int. Cl.
| | |
|---|---|
| *G01M 15/14* | (2006.01) |
| *G06T 7/00* | (2006.01) |
| *F01D 21/00* | (2006.01) |
| *G02B 23/24* | (2006.01) |
| *G01N 21/954* | (2006.01) |
| *G02B 13/06* | (2006.01) |
| *H04N 5/225* | (2006.01) |
| *G01M 15/02* | (2006.01) |

(52) U.S. Cl.
CPC ........... *G01M 15/14* (2013.01); *F01D 21/003* (2013.01); *G01N 21/954* (2013.01); *G02B 13/06* (2013.01); *G02B 23/2484* (2013.01); *G06T 7/0004* (2013.01); *G01M 15/02* (2013.01); *G06T 2207/10004* (2013.01); *G06T 2207/20221* (2013.01); *G06T 2207/30136* (2013.01); *H04N 2005/2255* (2013.01)

(58) Field of Classification Search
USPC ...................................................... 73/112.01
See application file for complete search history.

(56) References Cited

U.S. PATENT DOCUMENTS

| | | | |
|---|---|---|---|
| 5,349,850 A | * | 9/1994 | Young .................... G01B 11/00 73/112.01 |
| 5,563,650 A | | 10/1996 | Poelstra |

(Continued)

*Primary Examiner* — Eric S McCall

(57) ABSTRACT

A method of generating a comprehensive image (87) of interior surfaces (78, 80) of machine components such as a gas turbine combustor basket (59) and transition duct (34) by digitally stitching together multiple photographs (82) thereof, and analyzing the comprehensive image by contouring (91, 95A-B) of colors and shadings thereon, and quantifying and tracking aspects of the contours (A, B, C) over time for indications of degradation (89) of the interior surfaces. A scope (58) may be inserted into a port (56) in the combustor with a camera (72, 74) in a rotatable end (70) of the scope for obtaining a circumferential set (84) of photos at each axial position along a length of the combustor and transition duct. A 3D surface scanning device (76) in the scope may define the geometry of the interior surface for 3D photographic modeling thereof providing a virtual walk-through inspection.

18 Claims, 5 Drawing Sheets

(56) References Cited

U.S. PATENT DOCUMENTS

| | | | |
|---|---|---|---|
| 6,009,189 A | 12/1999 | Schaack | |
| 6,532,840 B2 | 3/2003 | Hatley et al. | |
| 6,542,230 B1 | 4/2003 | Luke | |
| 6,621,516 B1 | 9/2003 | Wasson et al. | |
| 6,867,586 B2 | 3/2005 | Hatcher et al. | |
| 6,992,315 B2* | 1/2006 | Twerdochlib | F01D 5/005 250/330 |
| 7,068,029 B2* | 6/2006 | Hatcher | G01N 27/902 324/239 |
| 7,489,811 B2* | 2/2009 | Brummel | G01N 21/8806 382/152 |
| 7,961,401 B1 | 6/2011 | Scott et al. | |
| 8,155,384 B2 | 4/2012 | Chew | |
| 8,184,151 B2* | 5/2012 | Zombo | F01D 21/003 348/82 |
| 8,299,785 B2 | 10/2012 | Bousquet et al. | |
| 8,786,848 B2 | 7/2014 | Hatcher et al. | |
| 2004/0051525 A1* | 3/2004 | Hatcher | G01N 27/902 324/262 |
| 2005/0073673 A1 | 4/2005 | Devitt et al. | |
| 2005/0199832 A1* | 9/2005 | Twerdochlib | F01D 5/005 250/559.29 |
| 2005/0200355 A1* | 9/2005 | Hatcher | G01N 27/902 324/239 |
| 2006/0088793 A1* | 4/2006 | Brummel | F23M 11/045 431/13 |
| 2007/0040911 A1 | 2/2007 | Riley | |
| 2007/0129604 A1* | 6/2007 | Hatcher | A61B 1/00048 600/136 |
| 2007/0157733 A1* | 7/2007 | Litzenberg | G01N 29/043 73/644 |
| 2012/0281084 A1* | 11/2012 | Hatcher | F01D 9/023 348/83 |
| 2013/0135457 A1* | 5/2013 | Kell | F01D 25/285 348/82 |
| 2013/0192353 A1* | 8/2013 | Hatcher | F01D 21/003 73/112.01 |
| 2013/0194412 A1* | 8/2013 | Hatcher | F01D 21/003 348/82 |
| 2013/0194413 A1* | 8/2013 | Hatcher | G02B 23/2476 348/82 |
| 2013/0235391 A1* | 9/2013 | Baleine | G01B 11/14 356/625 |
| 2013/0335530 A1 | 12/2013 | Hatcher, Jr. et al. | |
| 2013/0335549 A1* | 12/2013 | Hatcher, Jr. | G02B 23/2484 348/82 |
| 2015/0172565 A1* | 6/2015 | Haldeman | H04N 5/33 348/164 |
| 2015/0240657 A1* | 8/2015 | DeAscanis | F01D 21/003 416/1 |
| 2015/0241303 A1* | 8/2015 | DeAscanis | G01M 15/02 348/82 |
| 2016/0010496 A1* | 1/2016 | Hatcher, Jr. | F01D 21/003 415/13 |

* cited by examiner

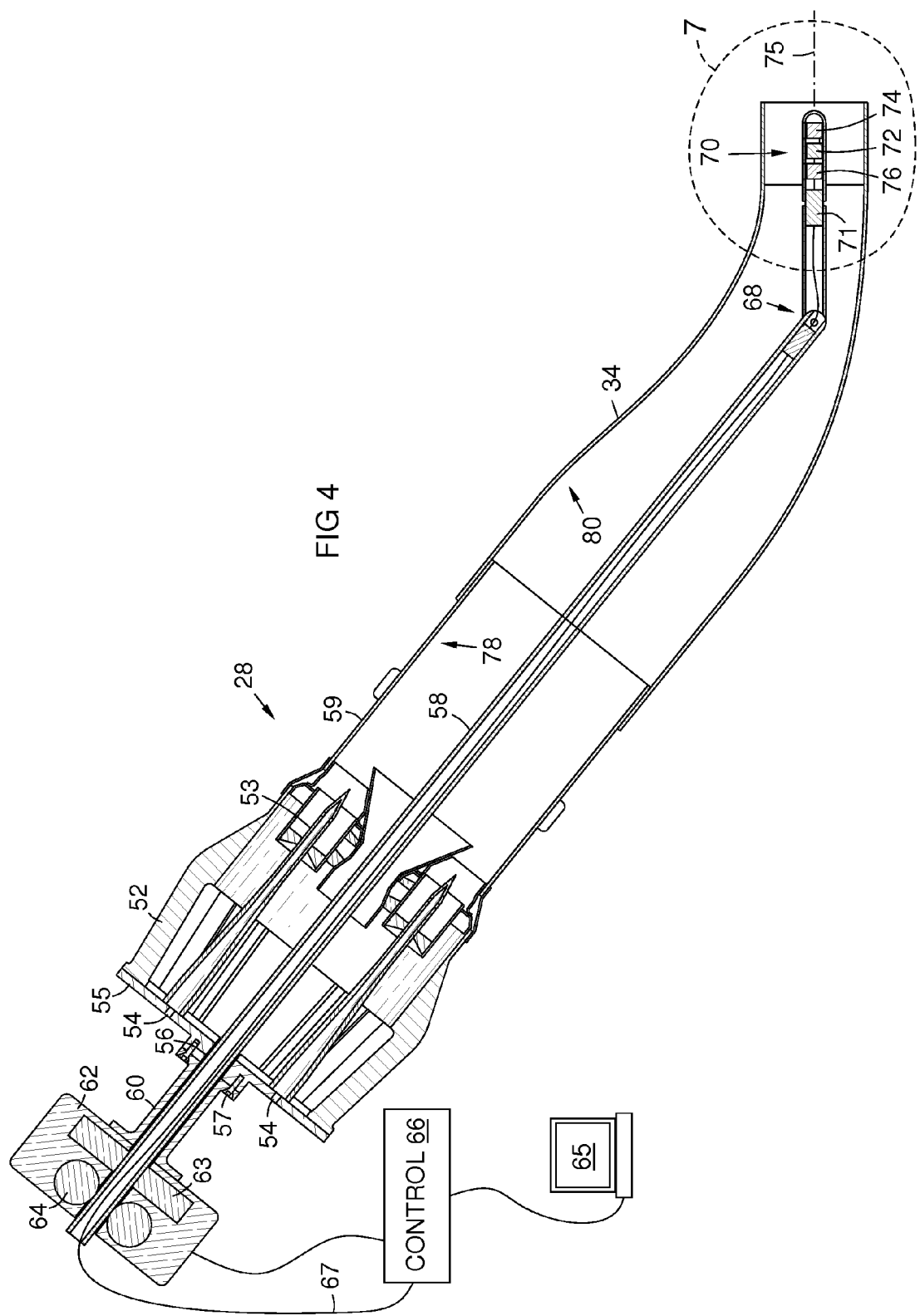

FIG 5A
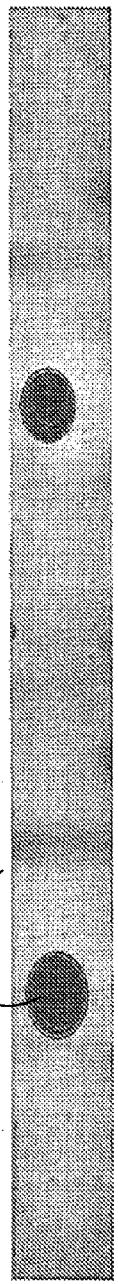
FIG 5B
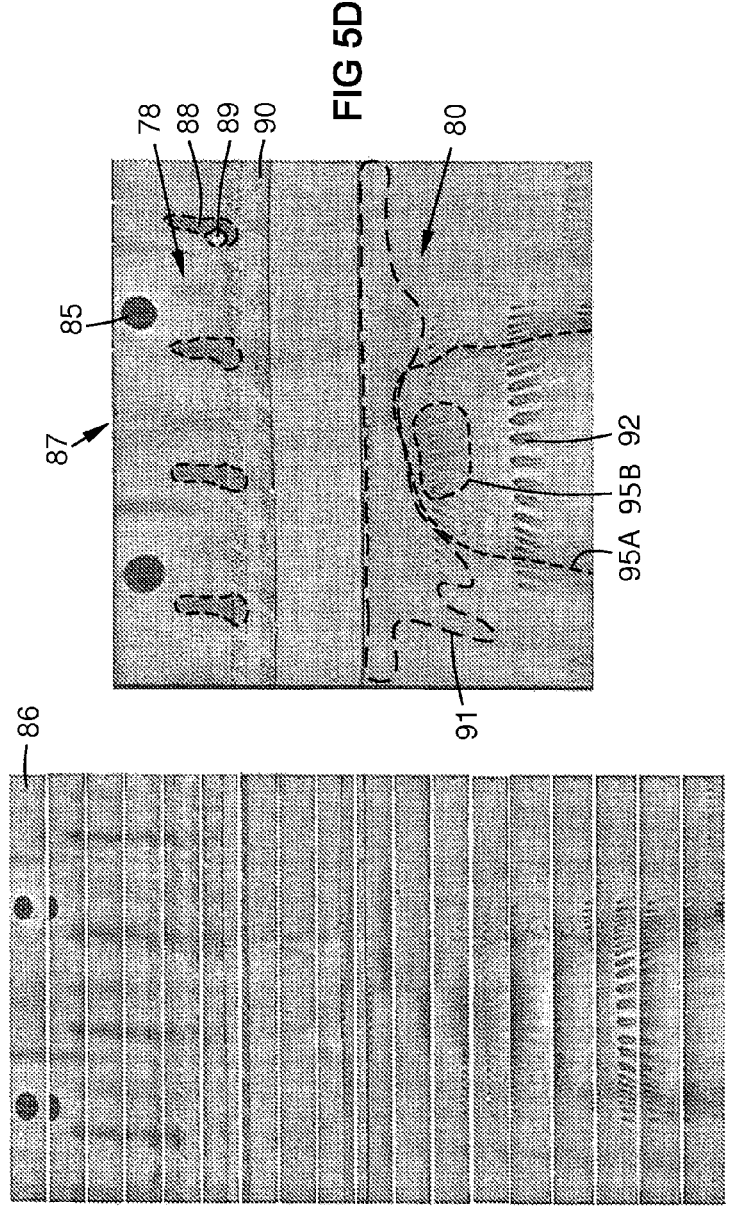
FIG 5D
FIG 5C

SIZE HISTORY OF TRACKED INTENSITY CONTOURS

INTERNAL INSPECTION OF MACHINERY BY STITCHED SURFACE IMAGING

This application is a continuation-in-part of U.S. patent application Ser. No. 13/972,000, filed 21 Aug. 2013 and published as US 2013/0335530 A1, which is incorporated by reference herein.

FIELD OF THE INVENTION

This invention relates to internal inspection of machinery, and more particularly to internal imaging and evaluation of power generating components including gas turbine combustor baskets and transition ducts.

BACKGROUND OF THE INVENTION

Internal surfaces of gas turbine combustors and transition ducts have been inspected using a scope camera inserted through the pilot nozzle port after removal of the pilot nozzle. This provides access for the scope through the center of the combustor cap into the combustion chamber basket and transition duct. However, previous camera inspection systems produce on the order of 300 individual photos of the interior surfaces of each combustor basket/transition. Position data may be stored with each image, but it is difficult and time consuming to make comparisons among these numerous small overlapping images in order to visualize the interior surface topography and any coloration or shading changes over larger areas than each individual photo. Visualization is complicated by the non-cylindrical shape of transition ducts, which causes image distortion from the angles of the inner surface relative to the camera.

BRIEF DESCRIPTION OF THE DRAWINGS

The invention is explained in the following description in view of the drawings that show:

FIG. 4 is side sectional view of an inspection scope inserted into a gas turbine combustor and transition duct according to aspects of an embodiment of the invention.

FIG. 5A is a sequence of photos taken around the circumference of the interior surfaces of a combustor basket and transition duct at a given axial position.

FIG. 5B is a circumferential panoramic image created by stitching the photos of FIG. 5A together.

FIG. 5C is a series of circumferential panoramic images as in FIG. 5B taken at successive axial positions in the combustor basket and transition duct.

FIG. 5D is a comprehensive image formed by stitching the circumferential panoramic images of FIG. 5C together.

DETAILED DESCRIPTION OF THE INVENTION

Figure 1:
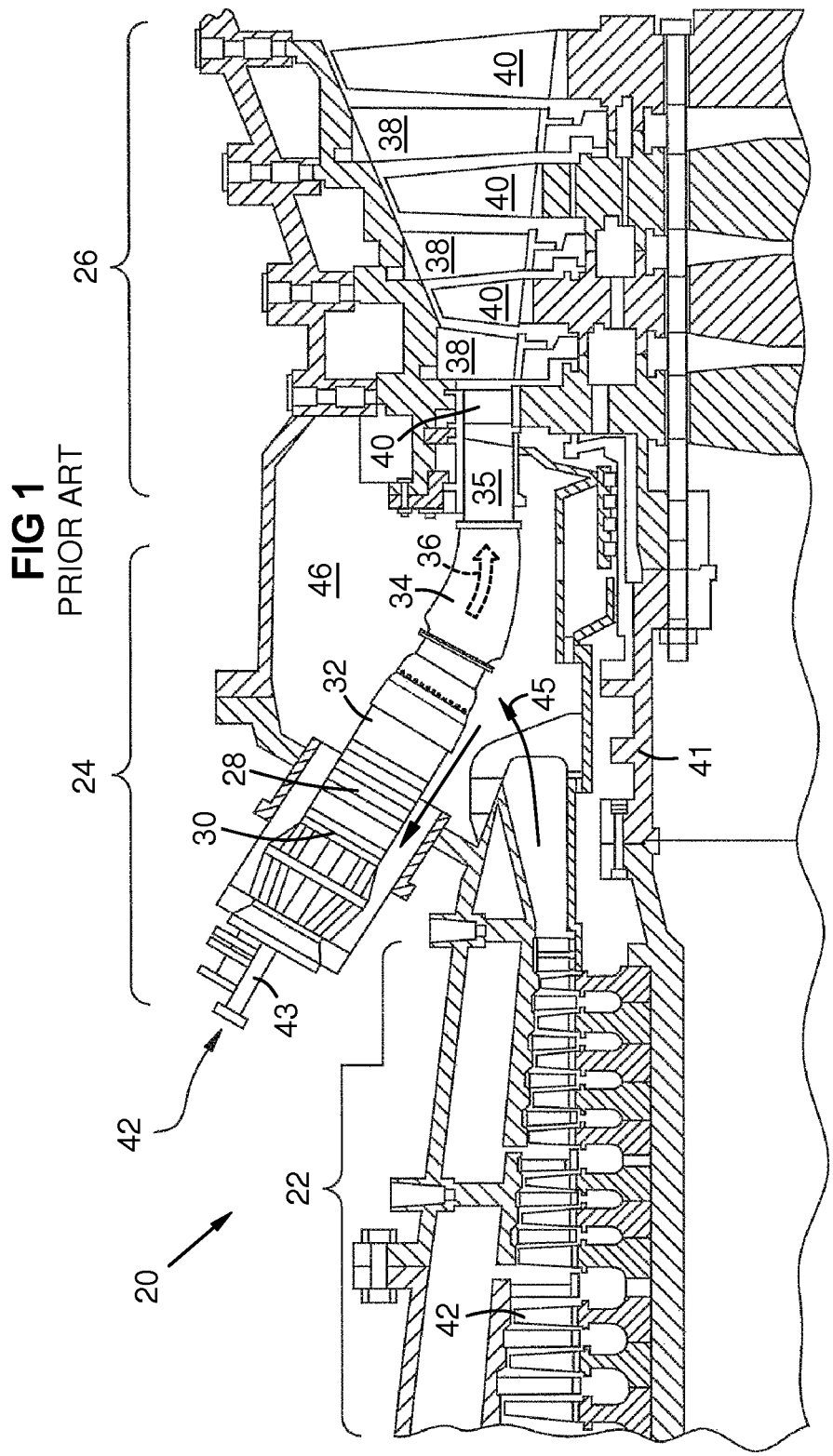
FIG. 1 is a partial side sectional view of a gas turbine engine known in the art.

FIG. 1 is a partial side sectional view of a gas turbine engine 20 with a compressor section 22, a combustion section 24, and a turbine section 26 as known in the art. One of the combustors 28 of a circular array of combustors in a can-annular arrangement is shown. Each combustor 28 has an upstream end 30 and a downstream end 32. A transition duct 34 and an exit piece 35 thereof transfer the combustion gas 36 from the combustor to the first row of airfoils 40 of the turbine section 26, which includes stationary vanes and 38 rotating blades 40. Compressor blades 42 are driven by the turbine blades 40 via a common shaft 41. Fuel 42 enters each combustor via a central pilot fuel nozzle 43, and via other supply tubes to a circular array of premix injectors. Compressed air 45 enters a plenum 46 around the combustors. It enters the upstream end 30 of the combustors, and is mixed with the fuel therein for combustion. The compressed air 45 also surrounds the combustors 28 and transition ducts 34 to provide cooling air thereto. It has a higher pressure than the combustion gas 36 in the combustor and in the transition duct.

Figure 2:
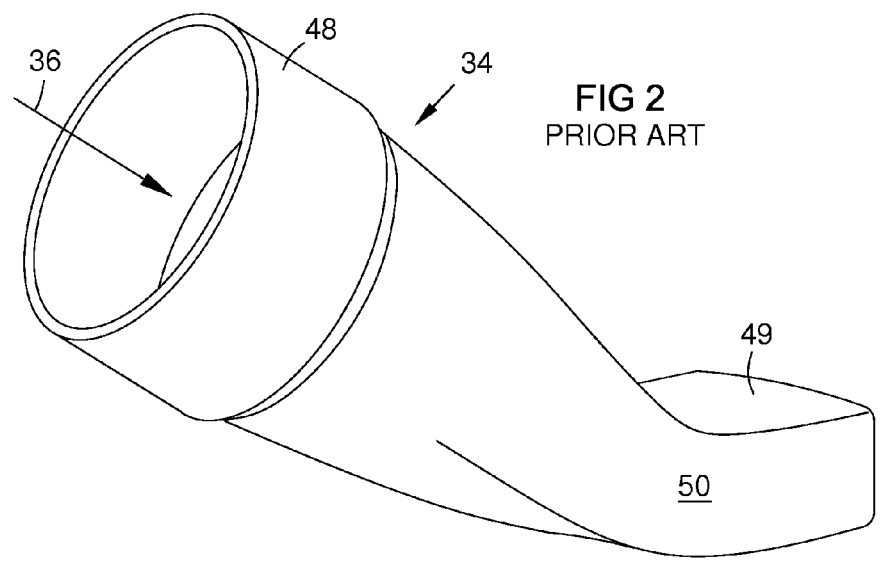
FIG. 2 is a perspective view of a transition duct known in the art.

FIG. 2 shows a transition duct 34 with an upstream end 48 that receives combustion gas 36 from the combustor. The upstream end 48 may be cylindrical. The downstream end 49 may be non-cylindrical such a generally rectangular. The duct body may have a substantial curvature 50.

Figure 3:
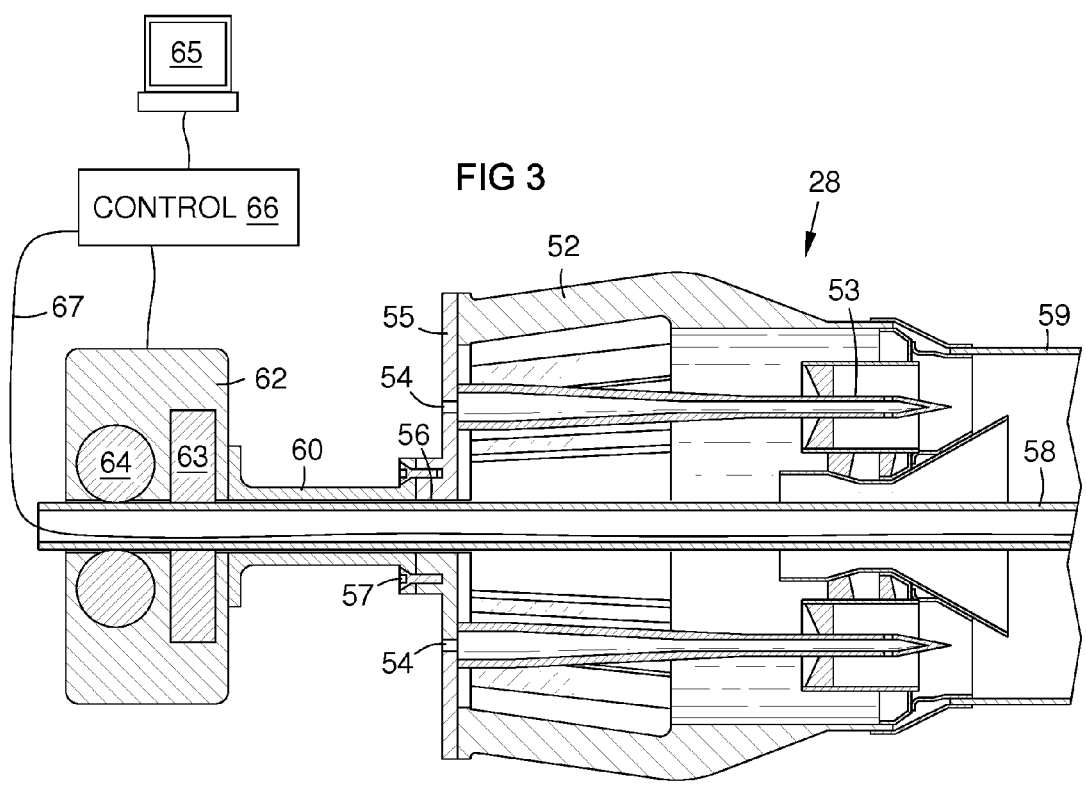
FIG. 3 is side sectional view of an inspection scope inserted into a gas turbine combustor according to aspects of an embodiment of the invention.

FIG. 3 is sectional side view of a combustor 28 with support legs 52, between which compressed air 45 (FIG. 1) enters to mix with fuel that is supplied to premix injectors 53 via fuel ports 54 in a mounting plate 55. Some detail is omitted for clarity, including supply lines to the fuel ports. A central fuel port 56 receives a pilot fuel nozzle 43 (FIG. 1), which is removed here. In its place, a camera boom or scope 58 is inserted for internal inspection of the combustor basket 59 and transition duct. Details of such camera systems are provided in the parent US patent application.

An inspection system housing 60 may be mounted to the pilot fuel port 56 by a mechanism normally used to mount the pilot fuel nozzle—for example by a threaded collar and/or machine screws 57. A scope positioning drive 62 may include a scope rotation drive 63 and translation drive 64. The rotation drive is optional if the distal end of the scope rotates as later described. A computer/controller 66 may control these drives. An interactive computer station 65 may provide operator control and computer graphics for human analysis. Control signal lines and power conductors may be provided through the interior of the scope. Control and power lines 67 may be provided to one or more cameras, lights, and distal actuators in the scope. Such lines 67 may include electrical conductors and, in some embodiments, optical fibers. The combustor 28 as shown is illustrated for reference, and is not a limitation except as claimed.

FIG. 4 is a sectional view of a scope 58 mounted as shown in FIG. 3, inserted into and through a combustor 28 and transition duct 34. The scope may have one or more motor controlled articulations 68, such as detailed in the parent US patent application. The end 70 of the scope may be rotatable by a motor 71 for scanning and imaging 360 degrees around the circumference of the inner surfaces 78, 80 at a given axial position. Herein "axial position" means a position along the axis 75 of the distal portion 70 of the inspection scope, which may substantially align with the 3D geometric centerline of the interior surfaces 78, 80 as much as possible. The end portion 70 may enclose a device such as camera 72, and may further include a lens 74 such as a galvanometer actuated mirror that pivots on an axis normal to the axis 75 of the end 70 of the scope. One or more lights 76 may be provided for the camera. Other embodiments are taught in the parent US patent application.

FIGS. 5A-D illustrate a process of stitching photos of the inner surfaces 78, 80 into a comprehensive view for analysis. FIG. 5A is a sequence or set 84 of photos 82 taken around the circumference of the interior surfaces of a combustor basket and transition duct at a given axial position. FIG. 5B is a circumferential panoramic image 86 created by stitching the photos 82 of FIG. 5A together. FIG. 5C is a series of circumferential panoramic 86 images as in FIG. 5B taken at successive axial positions in the combustor basket and transition duct. FIG. 5D is a comprehensive image 87 formed by stitching the circumferential panoramic images of FIG. 5C together and eliminating overlaps. This comprehensive image visually clarifies aspects of the surfaces that are unclear in the individual photos 82. For example, darker shaded areas 88 may indicate normal carbon deposits. Lighter areas 89 within a dark area may indicate a hot spot where carbon is burned away. Although not visible in black and white, a diffuse yellow coloration is present, especially in the dashed area 91 shown, which may indicate oxidation. Another area 95A has a slight blue tint with a slightly higher intensity in area 95B. Such colorations and shadings may be contoured by computer for analysis.

An engineering model of the combustor assembly may be used to identify and image features caused by structures such as crosslink tubes 85, acoustic damper holes 90, and film cooling holes 92, and subtract/ignore such features when creating surface contours 89, 90, 91, 95A-B. Alternately, the structural features 85, 90, 92 may be contoured in addition to the surface contours so that changes in shape or position of the structures can be analyzed. Static analysis of the comprehensive image may be performed based on absolute intensity limits, contour gradient limits, contour jaggedness, and contour overlaps—for example, a white area overlapping grey or grey overlapping yellow. The contours may be tracked over successive inspections. Quantified aspects of the tracked contours may be graphed in a time series to show the rates and accelerations of degradation as later shown. This analysis may be used to adjust or preempt a maintenance schedule. In general, shading and colors may be analyzed to indicate wear and condition characteristics of the gas path surfaces, including any thermal barrier coating thereon. A jagged contour may indicate exfoliation or spelling of the thermal barrier coating due to age, environment, structural flaws, or overheating.

In another method utilizing the invention, a thermal indicator paint may be applied to the inner surfaces 78, 80 prior to assembling the combustor section, either in original production or after disassembly for maintenance. A test run of the engine may be performed for a limited time to bring the surfaces to operating temperatures. The engine may then be shut down, and the inner surfaces examined in accordance with the present invention. The thermal paint will then display the heat topography at the operating temperatures as a color topography. This indicates whether a new engine design, or a maintenance re-assembly, or a modification meets specifications for thermal limits, and if an engine is operating properly. By using the present invention, there is no need to disassemble the combustors to inspect the thermal paint response. Subsequently, after a period of engine operation, the thermal paint burns away, and the previously described time series of inspections may be performed without thermal paint.

Figure 6:
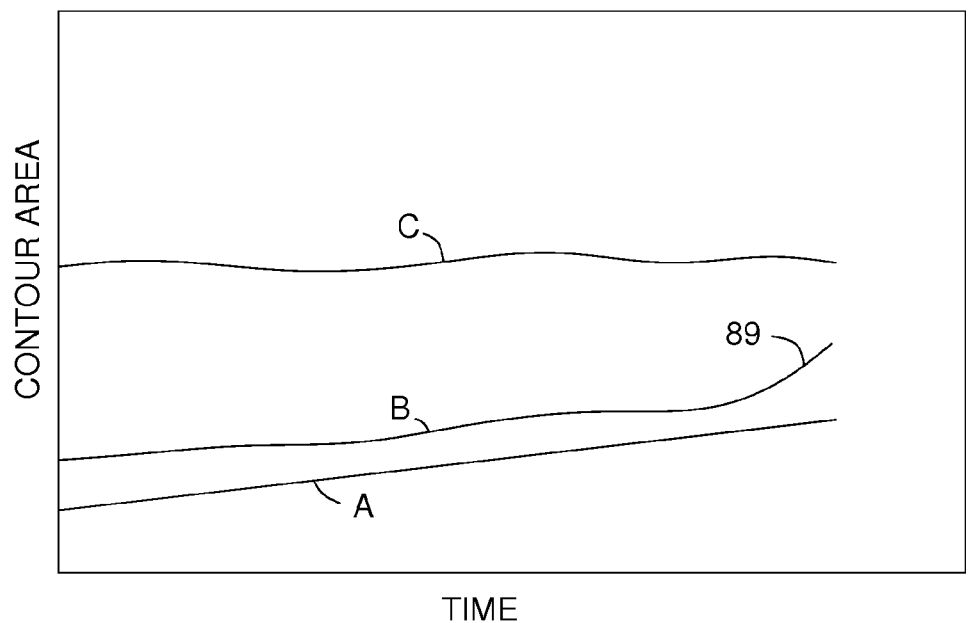
FIG. 6 is a size history of three intensity contours tracked over time.

FIG. 6 illustrates a time series of the sizes of three different intensity contours A, B, and C over a sequence of inspections. Contour A shows normal wear, Contour C shows no wear or degradation. Contour B shows a recent acceleration 89 in degradation above a predetermined acceleration threshold, causing an automated alert from the computer. The individual contours A, B, C may be identified and tracked over time using known algorithms, for example as used for weather radar tracking of storm cells and their intensities over time to compute local rainfall. The shapes of such contours may be quantified in terms of jaggedness, aspect ratio, or other factors. Such quantifications allow a high degree of automatic analysis that can bring timely attention to particular areas by computerized alerts, which may be presented for example as an audible alert and a flashing contour.

Figure 7:
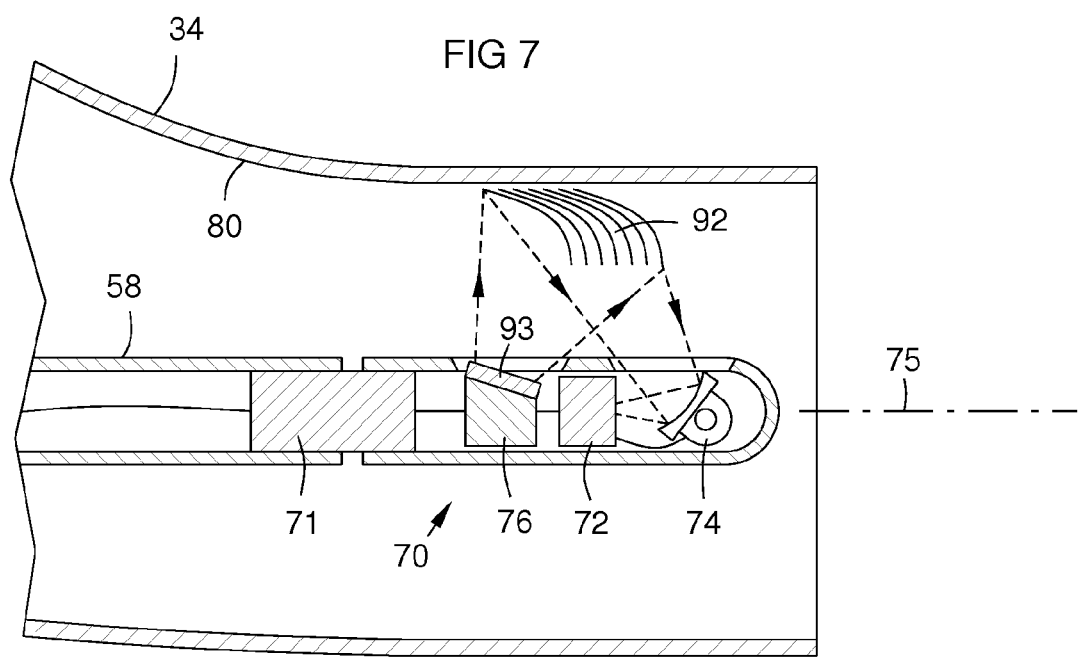
FIG. 7 is an enlarged side sectional view of the end of the scope of FIG. 4.

FIG. 7 shows an enlarged side sectional view of the distal end 70 of the scope 58 of FIG. 4. A camera sensor 72 such as a charge coupled device or other image sensor receives an image directed from a galvanometer-controlled mirror 74. A light source 76 projects a pattern 92 onto the inner surface 80 of the transition duct 34 for surface definition by the computer/controller as described in the parent US patent application. A liquid crystal panel 93 in the light/projector 76/93 may define the pattern and alternately clear to allow non-patterned light to illuminate the surface for photography as in FIG. 5A. Alternately, separate lights may be provided for pattern projection and photographic illumination. Surface scanning defines a precise surface contour relative to the camera for each image 82. The surface 80 can be accurately reconstructed in three dimensions as a digital model by known pattern projection and triangulation between the projector and the receiving mirror or lens 74. The photographic illuminating light may be white and/or a succession of different colors to enhance respective different aspects of the surface 80. As an alternative to a pattern projector 93, a triangulating laser surface scanner may be provided for defining the surface 80 in three dimensions. Such scanners can image a surface in 3 dimensions to a precision of tens of microns or thousandths of an inch, and thus can define surface roughness as an additional aspect of the comprehensive image for analysis.

By defining the surface relative to the camera, distortions due to camera angle can be removed by known algorithms. The surface image can then be transformed into a digital 3D visible surface rendering using known algorithms, allowing human inspectors to interactively "walk through" the combustor basket and transition duct via computer graphics for inspection, which may be color enhanced. An exemplary 3D scanning image processing software program is the "MeshLab" package of open source software that is downloadable via the Internet from the National Research Council of Italy Visual Computing Lab. Another source for exemplary 3D scanning image processing software is Geomagic of Research Triangle Park, N.C., USA.

In one embodiment, the comprehensive image may be mapped onto an engineering model of the interior surface to create a digital visual model of the interior surface in a computer for interactive walk-through viewing. Image distortions due to camera angle may be removed by defining the surface angles with a surface scanner as previously described and/or by fitting the comprehensive image to known surface features in the engineering model such as holes in the surface.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

The invention claimed is:

1. A method of inspecting an interior surface of a component of a gas turbine engine comprising:
   inserting a scope into an inner portion of the component without removing the component from the engine;
   obtaining a first set of circumferential photographs around a circumference of the interior surface at a given axial reference position therein with a camera on a distal end of the scope; and
   digitally stitching the first set of photographs to form a stitched view of the interior surface at the given axial reference position.

2. The method of claim 1, further comprising;
   removing a pilot fuel nozzle from a pilot fuel port of a combustor installed on the gas turbine engine;
   inserting the scope into the combustor via the pilot fuel port; and
   rotating the camera on the distal end of the scope over 360 degrees at the axial reference position.

3. The method of claim 1, further comprising:
   obtaining further sets of circumferential photographs at respective further axial reference positions;
   stitching the first and further sets of circumferential photographs of the interior surface to form a comprehensive image of the interior surface; and
   determining a condition of the interior surface by analysis of the comprehensive image for indications of use and degradation of the interior surface.

4. The method of claim 3, further comprising mapping and projecting the comprehensive image onto a three-dimensional engineering model of the interior surface, creating a digital visual model of the interior surface in a computer.

5. The method of claim 3, further comprising defining a three-dimensional geometry of the interior surface by scanning the interior surface with a 3D surface scanner in the distal end of the scope, and digitally modeling the interior surface in three dimensions by mapping the comprehensive image onto the three-dimensional geometry of the interior surface creating a digital visual model of the interior surface in a computer for interactive viewing.

6. The method of claim 5, further comprising:
   creating a degree of roughness contour on the comprehensive image by computerized contouring of a roughness of the interior surface defined by the 3D scanner, and
   further quantifying the indications of use and degradation of the interior surface by computer analysis of the degree of roughness contour.

7. The method of claim 3, further comprising:
   creating a set of intensity contours on the comprehensive image by computerized contouring of colors and shadings in the comprehensive image, and
   quantifying the indications of use and degradation of the interior surface by computer analysis of the set of intensity contours.

8. The method of claim 7, wherein the quantifying comprises computing an area within each contour, computing gradients and overlaps of the contours, and computing a shape aspect of each contour.

9. The method of claim 7, further comprising indicating an alert status by computerized flashing of one of the contours on the comprehensive image.

10. A method of evaluating a condition of an interior surface of a gas turbine combustor and transition duct, comprising:
    creating a sequence of comprehensive images of the interior surface over a respective time sequence of successive digital camera inspections of the gas turbine combustor;
    generating by computer a set of color and shading intensity contours on each of the comprehensive images;
    identifying and tracking by computer ones of the contours over successive ones of the comprehensive images;
    plotting a time series of a size of each tracked contour; and
    evaluating by computer the time series for indications of degradation of the interior surface.

11. The method of claim 10, further comprising providing a computerized alert when an acceleration of a degradation rate is found in the time series.

12. The method of claim 10, further comprising performing computerized identification of aspects of size, gradient, shape, and overlap of the contours, and computerized analysis of said aspects for the indications of degradation of the interior surface.

13. The method of claim 10, further comprising forming each comprehensive image by obtaining a circumferential sequence of photographs around a circumference of the interior surface at each of a sequence of axial positions along a 3D centerline of the interior surface; and digitally stitching the photographs together.

14. The method of claim 13, further comprising;
    removing a pilot fuel nozzle from a pilot fuel port of the gas turbine combustor;
    inserting a scope into the combustor via the pilot fuel port;
    rotating a camera on a distal end of the scope around the circumference of the interior surface at each of the sequence of axial positions to obtain each circumferential sequence of photographs.

15. The method of claim 13, further comprising defining a three-dimensional geometry of the interior surface by scanning the interior surface with a 3D surface scanner in the distal end of the scope, and digitally modeling the interior surface in three dimensions by mapping the comprehensive image onto the three-dimensional geometry of the interior surface creating a digital visual model of the interior surface in a computer for interactive viewing.

16. The method of claim 15 further comprising performing computerized analysis of a degree of a roughness of the interior surface as defined by the 3D scanner.

17. A method for evaluating a condition of an interior surface of a component in a gas flow path of a gas turbine, comprising:
    forming a comprehensive image of the interior surface over a circumference and a length thereof by digitally stitching a plurality of individual images of the interior surface obtained from a device on a scope inserted into the component; and
    determining the condition of the interior surface by creating contours of colors in the comprehensive image and analyzing the contours thereof for indicators of the condition of the interior surface.

18. The method of claim 17, further comprising:
    before forming the comprehensive image, painting the interior surface with a thermal imaging paint, and starting and running the gas turbine; and
    stopping the gas turbine, and forming the comprehensive image.

* * * * *